(12) United States Patent  (10) Patent No.: US 7,578,835 B2
Wang et al.  (45) Date of Patent: Aug. 25, 2009

(54) APPARATUS AND METHODS FOR BONE FRACTURE REDUCTION AND FIXATION

(75) Inventors: Robert C. Wang, Las Vegas, NV (US); Mohamed B. Trabia, Las Vegas, NV (US)

(73) Assignee: Board of Regents of the Nevada System of Higher Education, Reno, NV (US)

( * ) Notice: Subject to any disclaimer, the term of this patent is extended or adjusted under 35 U.S.C. 154(b) by 0 days.

(21) Appl. No.: 11/439,601

(22) Filed: May 24, 2006

(65) Prior Publication Data

US 2006/0235407 A1  Oct. 19, 2006

Related U.S. Application Data

(63) Continuation-in-part of application No. 10/293,732, filed on Nov. 12, 2002, now Pat. No. 7,235,077.

(60) Provisional application No. 60/350,785, filed on Nov. 9, 2001.

(51) Int. Cl.
 *A61B 17/80* (2006.01)
(52) U.S. Cl. ........................ 606/286; 606/902
(58) Field of Classification Search ......... 606/213–216, 606/280, 281–286, 291, 70–71, 57, 74, 105, 606/301, 902–906, 916; 623/17.17–17.19
See application file for complete search history.

(56) References Cited

U.S. PATENT DOCUMENTS 3,203,098 A * 8/1965 Petraitis .................... 433/23
3,831,608 A * 8/1974 Kletschka et al.
3,983,878 A * 10/1976 Kawchitch ................. 606/167
4,583,541 A * 4/1986 Barry
4,889,110 A * 12/1989 Galline et al. .............. 606/916
4,905,679 A * 3/1990 Morgan
4,966,599 A * 10/1990 Pollock
5,108,397 A * 4/1992 White
5,324,291 A * 6/1994 Ries et al. .................. 606/71
5,330,476 A * 7/1994 Hiot et al.
5,704,936 A * 1/1998 Mazel ....................... 606/254

(Continued)

*Primary Examiner*—Thomas C Barrett
*Assistant Examiner*—James L Swiger
(74) *Attorney, Agent, or Firm*—Ryan A. Heck, J.D.; UNR-DRI Technology Transfer Office

(57) ABSTRACT

Apparatus to facilitate reduction and fixation of a fracture by drawing together the fracture by applying tension to a reduction wire are disclosed. These apparatus include a bone plate for the fixation of a fractured bone having a plurality of fastener openings so that the bone plate may be secured by a plurality of fasteners across a reduced fracture to fixate a reduced fracture. The bone plate is configured with a channel that receives a reduction wire so that the reduction wire may extend between the bone plate and a reduction wire mount such as a bone screw. Methods of use of the present invention include fastening the bone plate to a first side of the fracture, fastening a reduction wire mount to a second side of the fracture, fastening a reduction wire to the reduction wire mount, receiving the reduction wire in the channel, applying tension to the reduction wire to draw the bone plate and the reduction wire mount together thereby reducing the fracture, and fixating the fracture by fastening the bone plate to the second side of the fracture.

17 Claims, 9 Drawing Sheets

U.S. PATENT DOCUMENTS 5,766,176 A * 6/1998 Duncan
5,989,256 A * 11/1999 Kuslich et al.
5,993,448 A * 11/1999 Remmler
6,093,201 A * 7/2000 Cooper et al.
6,248,106 B1 * 6/2001 Ferree
6,258,091 B1 * 7/2001 Sevrain et al.
6,575,741 B2 * 6/2003 Campbell .................... 433/18
6,692,498 B1 * 2/2004 Niiranen et al.

* cited by examiner

APPARATUS AND METHODS FOR BONE FRACTURE REDUCTION AND FIXATION

CROSS REFERENCE TO RELATED APPLICATIONS

This present utility patent application is a continuation-in-part application of U.S. patent application Ser. No. 10/293,732 filed on Nov. 12, 2002, now U.S. Pat. No. 7,235,077, that, in turn, claims the priority and benefits of U.S. Provisional Application 60/350,785 filed Nov. 9, 2001. The entireties of U.S. patent application Ser. No. 10/293,732 and of U.S. Provisional Application 60/350,785 are incorporated herein by reference. A co-pending application filed on the same date, entitled "APPARATUS AND METHODS FOR BONE FRACTURE FIXATION," U.S. patent application Ser. No. 11/439,611, is also incorporated herein in its entirety by reference.

BACKGROUND OF THE INVENTION

1. Field of the Invention

The present invention relates to medical devices and, more particularly, to apparatus and methods for the reduction and fixation of fractures.

2. Description of the Related Art

When a fracture is repaired, the bone fragments are placed in appropriate alignment in an anatomically correct position (reduction). Following reduction of the fracture, the fracture is then fixated, meaning that the bone fragments are prevented from moving from the reduced placement during the healing process. Various apparatus such as bone plates, bone screws, and rods are used for fixation of bone fragments. Following fixation, the fracture is then allowed to heal. After the fracture has healed, the fixation apparatus may be removed or may be left permanently in the body.

Bone plates, which are typically thin and have a plurality of fastener openings for fastening by various fasteners such as bone screws to the bone surface, are often used in cranial and maxillofacial surgery. For example, the repair of mandibular fractures often involves reduction and fixation by various bone plate systems. A surgeon will likely require assistance from one or more additional surgeons or surgical assistants in order to effect repair of a mandibular fracture by using a bone plate or bone plating system. One and, sometimes, two assistants must hold the bone fragments in reduction while the surgeon fixates the fracture by fastening the bone plate or bone plate system. Large incisions may be required in order to surgically fix a mandibular fracture with a bone plate or bone plate system, which can result in damage to blood vessels, especially the blood vessels that supply the bone, thereby interfering with the bone healing process. Nerve damage may also occur. The bone plate must be shaped to fit the bone in the region of the fracture. The shaping and fitting process, which generally involves trial and error, is conducted in the operating theater by the surgeons, and can be time consuming thereby lengthening the time the patient spends under anesthesia. A bone plate does have the advantage of providing sufficient structural support across the fracture so that, when a bone plate or bone plate system is used to fixate a mandibular fracture, the patient may be able to resume some normal eating requiring mastication following the surgery.

Reduction of a fracture may also be accomplished using a reduction wire and bone screws. When a reduction wire and bone screws are used to reduce and fixate a fracture, two bone screws are placed in the bone, one bone screw on each side of the fracture. The bone screws are only partly tightened down. A wire loop in then passed around the bone screws such that the wire fits under the heads of the bone screws, the bone screws having been placed such that the wire is perpendicular to the fracture. The surgeon then reduces the fracture by applying tension to the reduction wire by pulling on the reduction wire, which draws the bone fragments together. After reduction of the fracture, the wire may be further looped around the bone screws. Then the bone screws are tightened to clamp the wire between the bone and the screw heads thereby fixating the fracture. Looping the wire around bone screws with countersink heads will further reduce the separation of the fracture because the tension in the wire is increased as the bone screws are tightened down and the wire loops around the bone screw shafts are pushed onto the conical countersink. Use of a reduction wire and bone screws has been described for reduction and fixation of a mandibular fracture. See, for example, R. Wang et al., *Arch. Otolaryngol. Head Neck Surg.* 124, (1998) pp 448-452. While Wang et al. describe the use of 24-gage stainless steel wire and 2 mm diameter, 4-6 mm in length monocortical bone screws placed 4 to 6 mm from the fracture, nails or other fasteners could be substituted for the bone screws and a variety of wires and other ligatures could also be used.

Unlike the installation of a bone plate, a single surgeon may perform a fracture reduction and fixation by using a reduction wire and bone screws. Use of a reduction wire and bone screws requires a smaller incision resulting in less nerve and vascular damage than installation of a bone plate. This procedure may be quicker than installation of a bone plate, which reduces the patient's time under anesthesia.

However, a non-chewing diet is required following the use of a reduction wire and bone screws for reduction and fixation of a mandibular fracture. Furthermore, reduction wire and bone screws may only be used to reduce and fixate certain types of fractures. A reduction wire and bone screws is best applied to simple fractures perpendicular to the cortices or with interlocking fracture surfaces. A reduction wire and bone screws is usually not applicable to the repair of comminuted fractures or to the repair of oblique unstable fractures where the reduction wire might tend to further distract the fragments. Oblique unstable fractures are usually best repaired using bone plates or other apparatus.

Existing bone plates and bone plate systems for internal reduction and fixation of fractures, such as mandibular fractures, require a large incision, multiple surgeons or a surgeon plus at least one assistant, and lengthy anesthesia with concomitant risks and insults to the body. Simpler apparatus, such as reduction wire and bone screws, may be installed quickly by a single surgeon with a smaller incision than that required for installation of a bone plate or bone plate system. However, use of a reduction wire and bone screws does not give the structural support that a bone plate or bone plate system gives so that, in the case of mandibular fractures, the patient must follow a restricted diet of foods that do not require chewing for several weeks following surgery. A reduction wire and bone screws cannot be used to repair certain types of fractures. A bone plate or bone plate system must be used. Thus, it is seen that currently available apparatus for fracture reduction and fixation have a variety of shortcomings. Therefore, a need exists for an apparatus that can be installed by a single surgeon, that minimizes the size of the required incision, that gives the support to the fracture of a bone plate, and that has the ability to fixate the range of fractures that may be fixated by a bone plate.

SUMMARY OF THE INVENTION

Apparatus and methods in accordance with the present invention may resolve one or more of the needs and shortcomings discussed above and will provide additional improvements and advantages as will be recognized by those skilled in the art upon review of the present disclosure.

This present invention provides a bone plate designed to span a bone fracture and to be mounted to a bone surface so as to fixate the fracture. The bone plate defines a first surface that is distal to a bone surface and configured to be biased against a bone surface, and the bone plate defines a second surface that is proximal to the bone surface. A plurality of fastener openings are disposed between the first surface and the second surface allowing the bone plate to be fastened to the bone surface by a plurality of fasteners.

The bone plate is configured to operate in conjunction with a reduction wire and a reduction wire mount to reduce and fixate a fracture. The reduction wire mount may be, without limitation, a bone screw, a pin, post, nail, or other fastener. The reduction wire may be a stainless steel wire or any such wire or ligature suitable for reduction of the fracture.

The bone plate includes a channel, where the channel may be a channel, groove, post, or the like. The channel is configured to receive and slideably retain the reduction wire so that the reduction wire may extend between the bone plate and the reduction wire mount and a tension force may be applied to the reduction wire.

The apparatus may be operated by fastening the bone plate to the first fracture side. The reduction wire mount is fastened to the second fracture side. The bone plate is positioned such that the bone plate would span the fracture upon reduction of the fracture and oriented so as to operate in conjunction with the reduction wire mount and reduction wire. A reduction wire is then looped around or otherwise attached to the reduction wire mount. The reduction wire is also received by the channel, so that the reduction wire extends between the reduction wire mount and the bone plate. A tension force is then applied to the reduction wire, which draws the bone plate and the reduction wire mount together, which draws the first fracture side and the second fracture side together, thereby reducing the fracture. Following reduction, the fracture may be fixated by fastening the bone plate, which now spans the fracture, to the second fracture side.

A single surgeon may be able to operate the apparatus. The apparatus according to the present invention may provide more support to the fixated fracture than the use of a reduction wire and bone screws. When an apparatus according to the current invention is used to treat mandibular fractures, a patient may be able to eat a more varied diet including foods that require chewing in contrast to treatment of a mandibular fracture by reduction wire and bone screws.

Other features and advantages of the invention will become apparent from the following detailed description, and from the claims.

Figure 1:
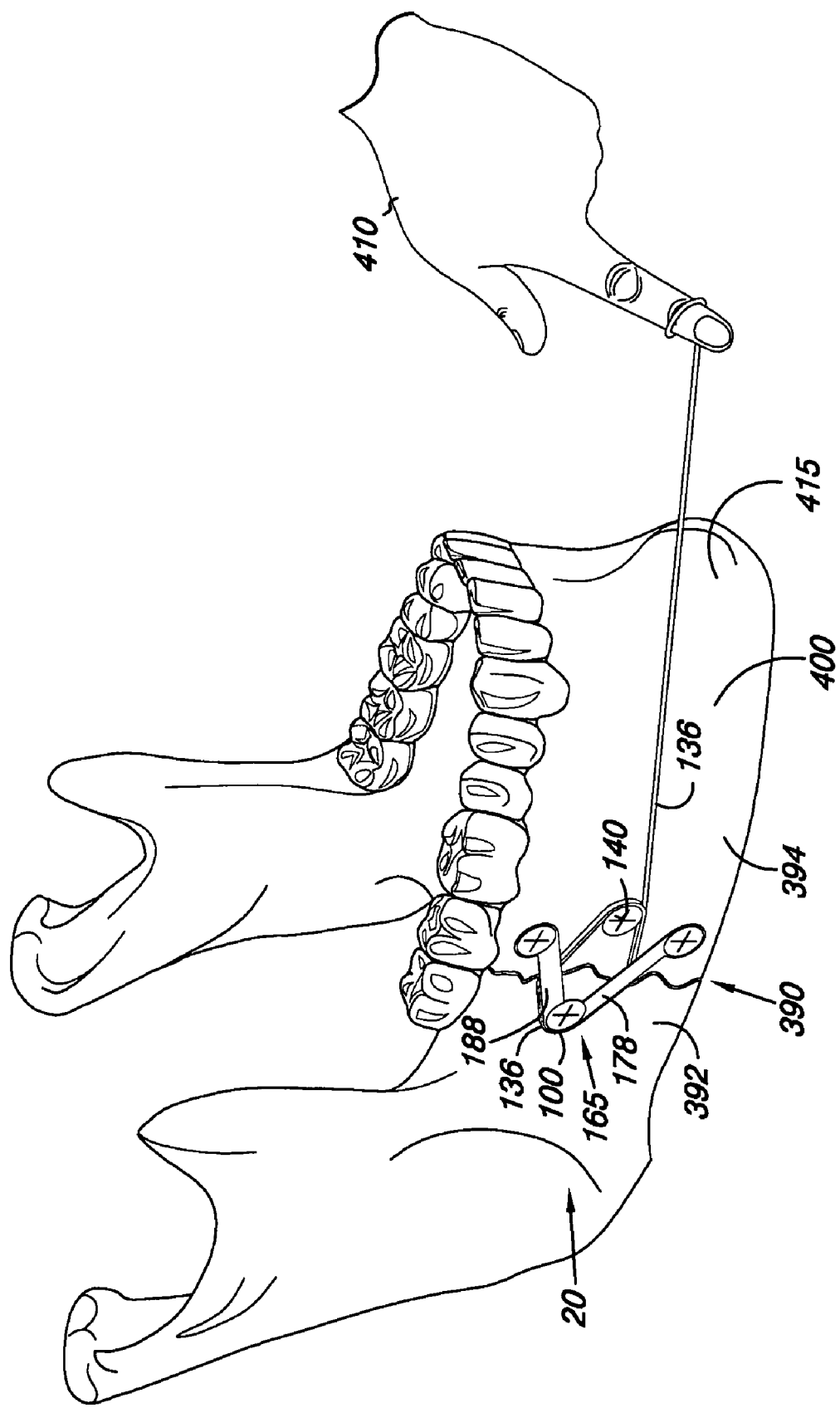
FIG. 1 illustrates a partial perspective view of an exemplary embodiment of an apparatus in accordance with the present inventions being applied to reduce and fixate a mandibular fracture.

All Figures are illustrated for ease of explanation of the basic teachings of the present invention only; the extensions of the Figures with respect to number, position, relationship and dimensions of the parts to form the embodiment will be explained or will be within the skill of the art after the following description has been read and understood. Further, the exact dimensions and dimensional proportions to conform to specific force, weight, strength, flow and similar requirements will likewise be within the skill of the art after the following description has been read and understood. Where used in various Figures, the same numerals designate the same or similar parts. Furthermore, when the terms "top," "bottom," "right," "left," "forward," "rear," "first," "second," "inside," "outside," and similar terms are used, the terms should be understood to reference only the structure shown in the Figures and utilized only to facilitate describing the illustrated embodiments. Similarly, when the terms "proximal," "distal," and similar positional terms are used, the terms should be understood to reference the structures shown in the Figures as they will typically be utilized by a physician or other user who is treating or examining a patient with an apparatus in accordance with the present invention.

DETAILED DESCRIPTION OF THE INVENTION

The present inventions provide an apparatus 20 for the fixation of a bone fracture 390 having a first fracture side 392 and a second fracture side 394. The apparatus includes a bone plate 100 capable of being secured by a plurality of fasteners 138 to a bone surface 400 through a plurality of fastener openings 142. The bone plate 100 is designed to span the bone fracture 390 so that the bone plate 100 may be fastened to the bone surface 400 on the first fracture side 392 and to the bone surface 400 on the second fracture side 394 of fracture 390 to fixate the fracture 390.

The bone plate 100 is configured to operate in conjunction with a reduction wire 136 and a reduction wire mount 140 to reduce and fixate the fracture 390. The reduction wire 136 may be a stainless steel wire or any wire or ligature suitable for reduction of the fracture 390. The reduction wire mount 140 may be, without limitation, a bone screw 220, a pin, a post, a nail, or other fastener. The bone plate 100 includes a channel 134 where the channel 134 is configured to receive and slideably retain the reduction wire 136. The channel 134 may be a channel, groove, slot, or the like. The bone plate 100, channel 134, reduction wire mount 140, and reduction wire 136 are configured so that placing the reduction wire 136 in tension draws the bone plate 100 and the reduction wire mount 140 toward one another when the bone plate 100 and reduction wire mount 140 are fastened to opposite sides of the fracture 390 and the reduction wire 136 is attached to the reduction wire mount 140 and received by the channel 134 so as to extend between the reduction wire mount 140 and the bone plate 100. Thus, placing the reduction wire 136 in tension draws the first fracture side 392 and the second fracture side 394 together, thereby reducing the fracture 390. Following reduction, the bone plate 100 may then be fastened to both sides of the fracture so as to fixate the fracture.

The apparatus 20 is used as follows. The bone plate 100 is fastened to the bone surface 400 on the first fracture side 392. The reduction wire mount 140 is fastened to the bone surface 400 on the second fracture side 394. The reduction wire 136 may be fastened to the reduction wire mount 140, for example, by looping the reduction wire 136 around the reduction wire mount 140. The reduction wire 136 is then received by the channel 134 such that the reduction wire 136 extends between the bone plate 100 and the reduction wire mount 140. A surgeon pulls on the reduction wire 136 placing the reduction wire 136 in tension thereby reducing the fracture 390 by drawing the bone plate 100 and the reduction wire mount 140 toward one another so that the first fracture side 392 and the second fracture side 394 are drawn together. Following reduction of the fracture 390, the bone plate 100 is fastened to the bone surface 400 on the second fracture side 394 to fixate the fracture 390.

Referring generally to the Figures, the apparatus 20 according to the present invention includes a bone plate 100 designed to work in conjunction with a reduction wire 136 and a reduction wire mount 140. The bone plate 100 defines a first surface 130 that is distal to the bone surface 400, and the bone plate 100 defines a second surface 132 that is proximal to the bone surface 400. The first surface 130 is configured to be received against the bone surface 400. The second surface 132 may be configured to be atraumatic, to receive tissue, and to maintain a low profile of the apparatus 20 over the bone surface 400. The first surface 130 of the bone plate 100 may be arcuate to conform to the shape of an arcuate bone surface 400, and the second surface 132 may or may not curve in conformity to an arcuate first surface 130. A thickness 126 may be defined as a distance between the first surface 130 and the second surface 132. The bone plate 100 may be of various thicknesses 126, and different regions of the bone plate 100 may have different thicknesses 126. The general preference is to minimize the thickness 126 to minimize the protrusion of the bone plate 100 above the bone surface 400 to which the bone plate 100 is applied.

A plurality of fastener openings 142 are disposed between the first surface 130 and the second surface 130 so that the bone plate 100 may be secured by a plurality of fasteners 138 to the bone surface 400 through the plurality of fastener openings 142. The fasteners 138 may be bone screws 220, nails, pins, adhesives, or other fasteners recognized by those skilled in the art. The fasteners 138 may be monocortical, bicortical, or combinations thereof. A variety of fasteners 138 may be used in combination. It will be appreciated, however, that the fastener openings 142 would not be present if the bone plate 100 is designed to be secured in other ways such as by various adhesives. The fastener openings 142 may be countersunk 144 so that fasteners 138 are flush with the second surface 132 in order to maintain a low profile of the bone plate 100. The countersinks 144 may be eccentric and oriented to force the bone plate 100 to move parallel to the bone surface 400 as the bone screw heads 226 engage the eccentric countersinks 144 when tightened, thereby increasing the reduction of the fracture 390.

The channel 134 may be configured into a surface of the bone plate 100. A first perimeter 128 bounds the first surface 130 and is defined by the limits of the first surface 130. A second perimeter 129 bounds the second surface 132 and is defined by the limits of the second surface 132. The limits of the bone plate 100 between the first surface 130 and the second surface 132 define at least one peripheral surface 131. The peripheral surface 131 may be a solid surface, or, at least a portion of the peripheral surface 131 may be defined by one or more discrete connectors such as posts where the discrete connectors such connect the portions of the bone plate that define the first surface 130 to the portions of the bone plate that define the second surface 132. The peripheral surface 131 may be, at least in part, perpendicular to the first perimeter 128 and perpendicular to the second perimeter 129 to conform to the face of a regular geometric figure, or the peripheral surface 131 may have various complex or irregular geometries. The peripheral surface 131 may, at least in part, lie within the first perimeter 128, or the peripheral surface 131 may, at least in part, extend beyond the first perimeter 128. The peripheral surface 131 may, at least in part, lie within the second perimeter 129, or the peripheral surface 131 may, at least in part, extend beyond the second perimeter 129. The first surface 130, the second surface 132, and the peripheral surface 131 may be configured to form a channel 134 or otherwise configured to receive a reduction wire 136 over a portion thereof.

The geometric configuration of the bone plate 100 depends upon the nature of the fracture 390 that the bone plate 100 is designed to fixate, recognizing that the bone plate 100 must span the fracture 390, must conform to the bone surface 400, and must lend sufficient structural support to the bone surface 400 to maintain fracture 390 fixation. The first perimeter 128 and the second perimeter 129 typically define a geometric configuration of the bone plate 100. The geometric configuration of the bone plate 100 may be that of a polygon, such as a rectangle, or may be other geometric configurations such as a "V," an "L," or a "U." Bone plates 100 having "Y" configurations, "H" configurations, and irregular configurations may also be constructed according to the present invention. Thus, it should be appreciated that the shapes in the Figures and otherwise disclosed are merely exemplary and are not a limitation of the shape of the bone plate 100 that may be constructed according to the present invention.

The bone plate 100 is configured to include a channel 134, the channel 134 being configured to receive and to slideably retain a reduction wire 136, the reduction wire 136 extending between the bone plate 100 and the reduction wire mount 140. The channel 134 may be, for example, a channel, a slot, a groove, a notch, a post, an eyelet, a plurality or combination thereof, or the like. The channel 134 may be internal so as to be disposed between the first surface 130 and the second surface 132. The channel may be external to the first surface 130 or the second surface 132. The channel 134 may be partly internal and partly external.

The reduction wire 136 may be any wire, cord, or ligature suitable in size, construction, and tensile strength for reducing the fracture 390. A 24-gage 304 stainless steel wire is a typical reduction wire 136 used for reducing mandibular fractures.

Typically, the reduction wire mount 140 is a bone screw 220, but the reduction wire mount 140 could be any type of fastener or post capable of receiving the reduction wire 136 during the reduction of fracture 390 such as screws or nails. The reduction wire mount 140 typically receives the reduction wire 136 by looping the reduction wire 136 around the reduction wire mount 140. However, upon review of the present disclosure, it would be readily recognized that the reduction wire mount 140 could be configured to facilitate receiving the reduction wire 136 in a variety of ways such as by including a groove, notch, eyelet, or channel in the reduction wire mount 140.

A bone screw 220 with a conical countersink 224 could be used as the reduction wire mount 140. Looping the reduction wire 136 around the bone screw shaft 222 can produce additional reduction of the fracture 400, because the tension in the reduction wire 136 is increased as the bone screw 220 type reduction wire mount 140 is tightened down and the reduction wire 136 loops around the bone screw shaft 222 are pushed onto the conical countersink 224.

The reduction wire mount 140 acts as a cantilever beam. Tension force in the reduction wire is transmitted to the bone through the reduction wire mount 140 as shear force and moment. The greater the distance from the bone surface 400 to the point of engagement between the reduction wire 136 and the reduction wire mount 140, the greater the moment that is transmitted to the bone. Positioning the channel 134 on the bone plate 100 and otherwise configuring the bone plate 100 such that the reduction wire 136 engages the reduction wire mount 140 near the point where the reduction wire mount 140 passes into the bone surface 400 minimizes the moment transmitted to the bone by the reduction wire mount 140 when the reduction wire 136 is placed in tension. The channel 134 should also be configured to protect the bone surface 400 from abrasion by the reduction wire 136.

The bone plate 100 may be configured to contact the reduction wire mount 140 or to avoid contact with the reduction wire mount 140. For example, the bone plate 100 may be configured to include a reduction wire mount 140 by defining an aperture 146. The aperture 146 passes through the bone plate 100 between the first side 130 and the second side 132, the aperture 146 being interior to the first perimeter 128 and interior to the second perimeter 129. The aperture 146 may have be configured to accommodate the reduction wire mount 140, for example, by being sized to bias against the reduction wire mount while allowing the reduction wire mount to slide within the aperture. The aperture may have an aperture side 147, which is configured to engage the reduction wire mount 140 when the reduction wire mount 140 is tightened against the aperture side 147. The reduction wire mount 140 may then be used to fasten the bone plate 100.

In some embodiments, the bone plate 100 may be configured so that at least a portion of the peripheral surface 131 slideably receives the reduction wire mount 140, biases against the reduction wire mount 140, or otherwise engages the reduction wire mount 140 when the reduction wire 136 is received by the channel 134 and the reduction wire mount 140 and the reduction wire 136 extends between the bone plate 100 and the reduction wire mount 140. The peripheral surface 131 may be configured to engage the reduction wire mount 140 when the reduction wire mount 140 is tightened against the peripheral surface 131 so that the reduction wire mount 140 may be used to fasten the bone plate 100.

In other embodiments, the bone plate 100 may be configured to maintain a gap 149 between the bone plate 100 and the reduction wire mount 140. The gap 149 is maintained when the reduction wire 136 is received by the channel 134 and the reduction wire mount 140 and the reduction wire 136 extends between the bone plate 100 and the reduction wire mount 140.

Other embodiments the bone plate 100 according to the present invention may have a plurality of channels 134 to accommodate one or more reduction wires 136 extending between the bone plate 100 and a plurality of reduction wire mounts 140. A single bone plate 100 could then be used to reduce and fixate a plurality of fractures 390.

The bone plate 100 may be, without limitation, solid, porous, composite, or may be a mesh or combinations thereof. The bone plate 100, the channel 134, the fasteners 138, the reduction wire mount 140, and the reduction wire 136, and other components of the apparatus 20 may be fabricated of biocompatible materials, as would be recognized by those skilled in the art. Examples of such biocompatible materials would include titanium, various stainless steel alloys, ceramics, plastics, composites, laminates, and bioabsorbable materials. These materials may be used exclusively or in combination.

An embodiment of the apparatus 20 according to the present invention is shown in FIG. 1. In FIG. 1, the bone plate 100 is shown as a "V" shaped structure 165 with a first arm 178 and a second arm 188. The bone plate 100 is fastened to a first fracture side 392 of a fracture 390 by a fastener 138 in a fastener 138 in a fastener opening 142. A reduction wire mount 140 is shown fastened to a second fracture side 394 of the fracture 390. A reduction wire 136 is fastened to the reduction wire mount 140. The reduction wire 136 is extended from the reduction wire mount 140 to the bone plate 100, received by the channel 134 of bone plate 100. The reduction wire 136 is further extended back to the reduction wire mount 140 such that the reduction wire 136 passes around a portion of the reduction wire mount 140 and is then grasped by a finger 410 of a surgeon. By pulling on the reduction wire 136, the surgeon places the reduction wire 136 in tension, thereby reducing the fracture 390 by drawing the bone plate 100 and the reduction wire mount 140 toward one another so that the first fracture side 392 and the second fracture side 394 are drawn together. Following reduction of the fracture 390, the bone plate 100 is fastened to the second side 394 of the fracture 390 using fasteners 138 so that the bone plate 100 is fastened to both the first side 392 and the second side 394 of the fracture 390 thereby fixating the fracture 390. Although a fracture of the mandibular bone 415 is shown in FIG. 1, it should be understood that an apparatus 20 according to the present invention may be used to reduce and fixate a variety of fractures including a variety of fractures of the various cranial-maxillofacial bones.

Several embodiments of apparatus 20 according to the present invention are shown in FIGS. 2A-2E. The apparatus 20 includes a bone plate 100. The bone plate 100 is designed to span a bone fracture 390 and to be fastened to a bone surface 400 on a first side 392 of fracture 390 and a bone surface 400 on a second side 394 of fracture 390 to fixate fracture 390. The bone plate 100 is configured with a channel 134 that slideably receives and retains a reduction wire 136, so that the reduction wire 136 may be fastened to a reduction wire mount 140 and received by the channel 134 such that the reduction wire 136 extends between the bone plate 100 and the reduction wire mount 140 and a tension force may be applied to the reduction wire 136.

As illustrated in FIGS. 2A-2E, the bone plate 100 has a first surface 130 that is distal to the bone surface 400 and a second surface 132 that is proximal to the bone surface 400. A first perimeter 128 bounds the first surface 130 and is defined by the first surface 130. A second perimeter 129 bounds the second surface 132 and is defined by the second surface 132. A peripheral surface 131 links the first perimeter 128 to the second perimeter 129. In these embodiments the first surface 130 and the second surface 132 are shown as flat, congruent, and oriented to one another such that the bone plate 100 has a regular geometric configuration.

Figure 2A:
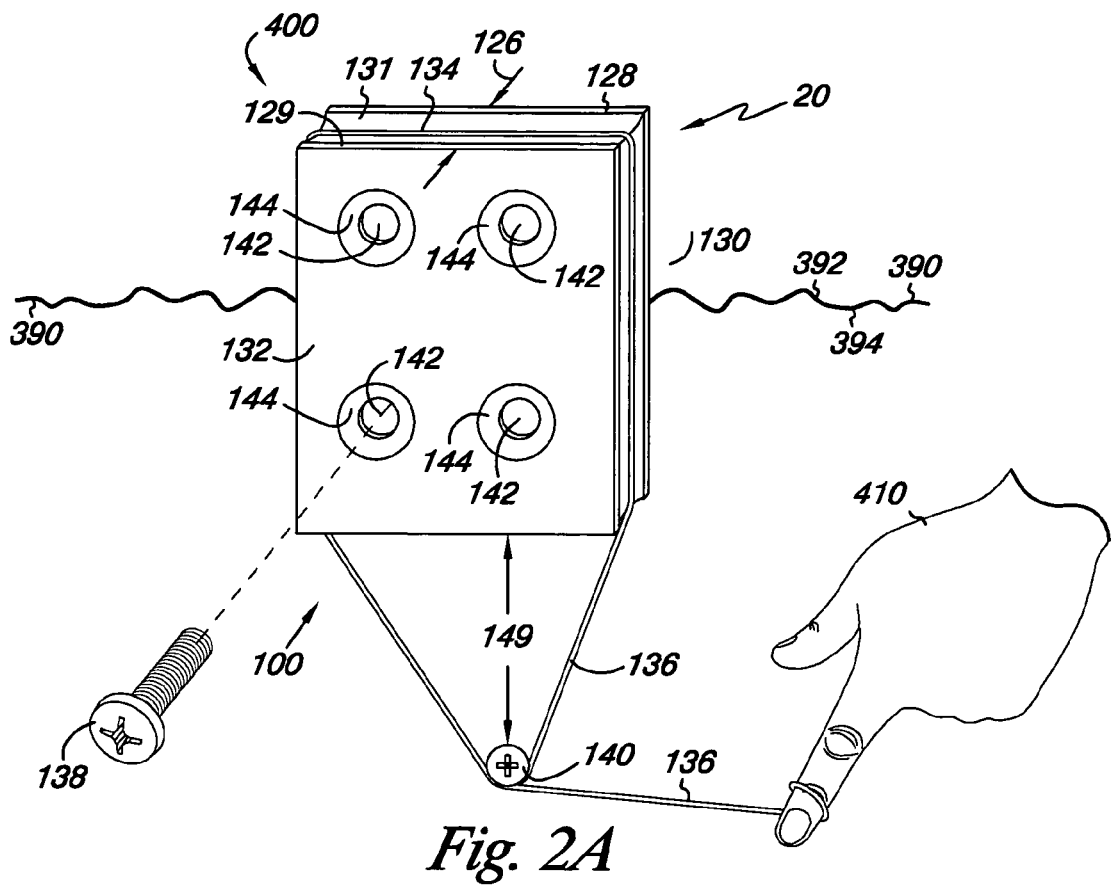
FIG. 2A illustrates a partial perspective view of an exemplary embodiment of an apparatus in accordance with the present inventions wherein the bone plate has a rectangular geometry and a channel receives a reduction wire so that the bone plate is connected to a reduction wire mount by the reduction wire.
Figure 2B:
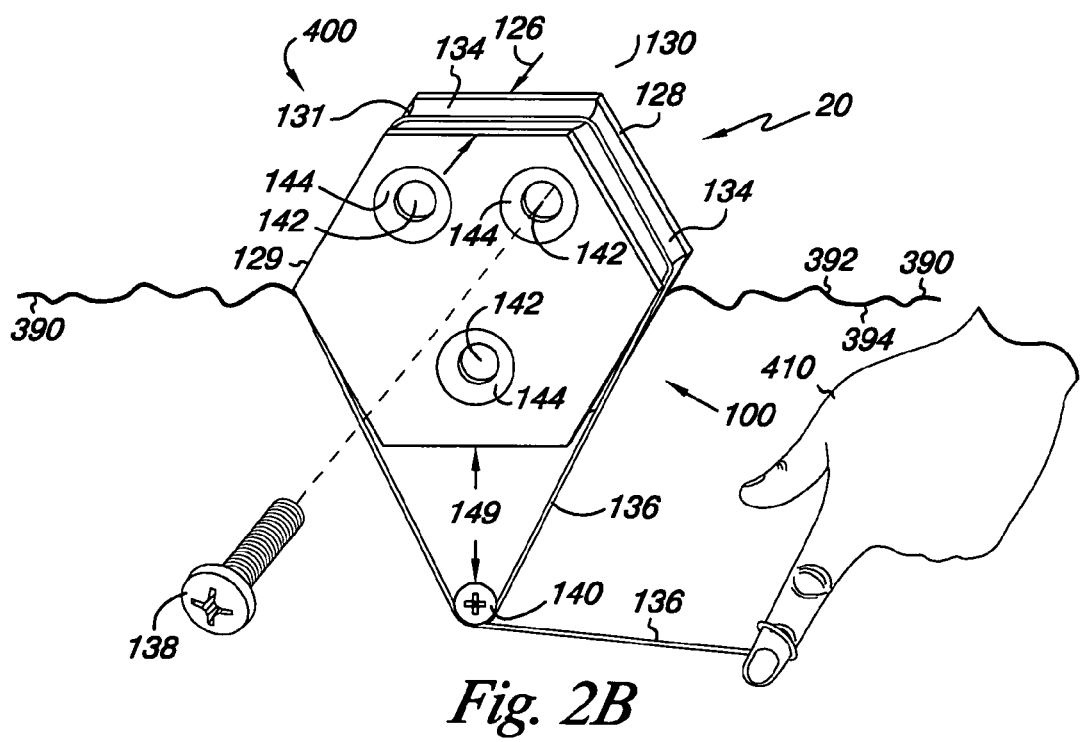
FIG. 2B illustrates a partial perspective view of an exemplary embodiment of an apparatus in accordance with the present inventions wherein the bone plate has a hexagonal geometry and a channel receives a reduction wire so that the bone plate is connected to a reduction wire mount by the reduction wire.
Figure 2C:
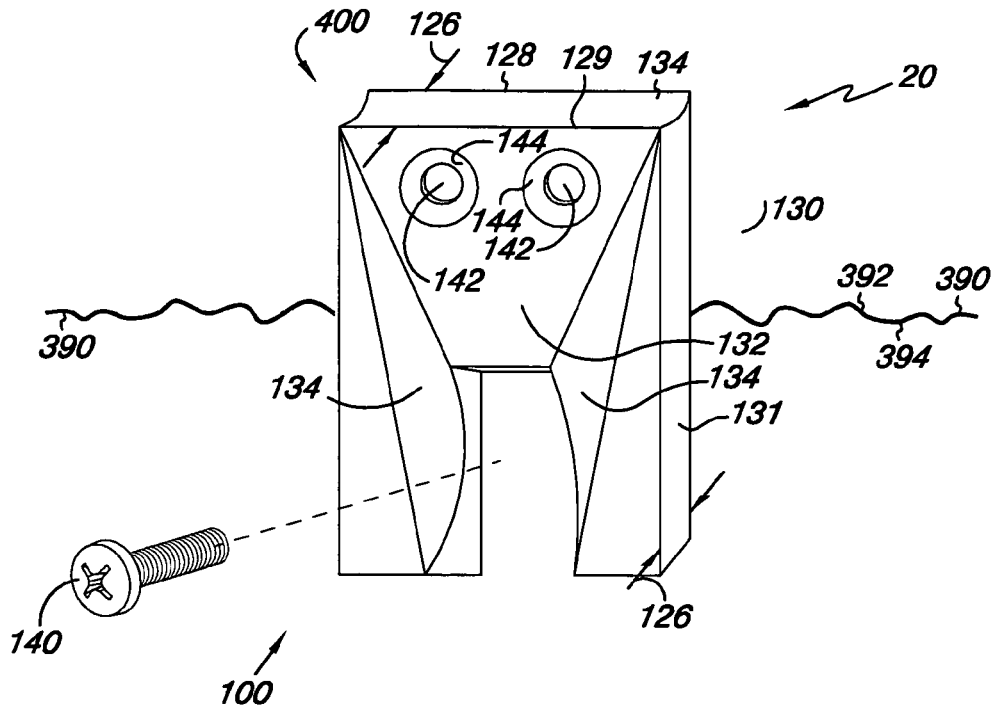
FIG. 2C illustrates a partial perspective view of an exemplary embodiment of an apparatus in accordance with the present inventions wherein the bone plate has a channel that receives a reduction wire and the peripheral surface is configured to engage a reduction wire mount.
Figure 2D:
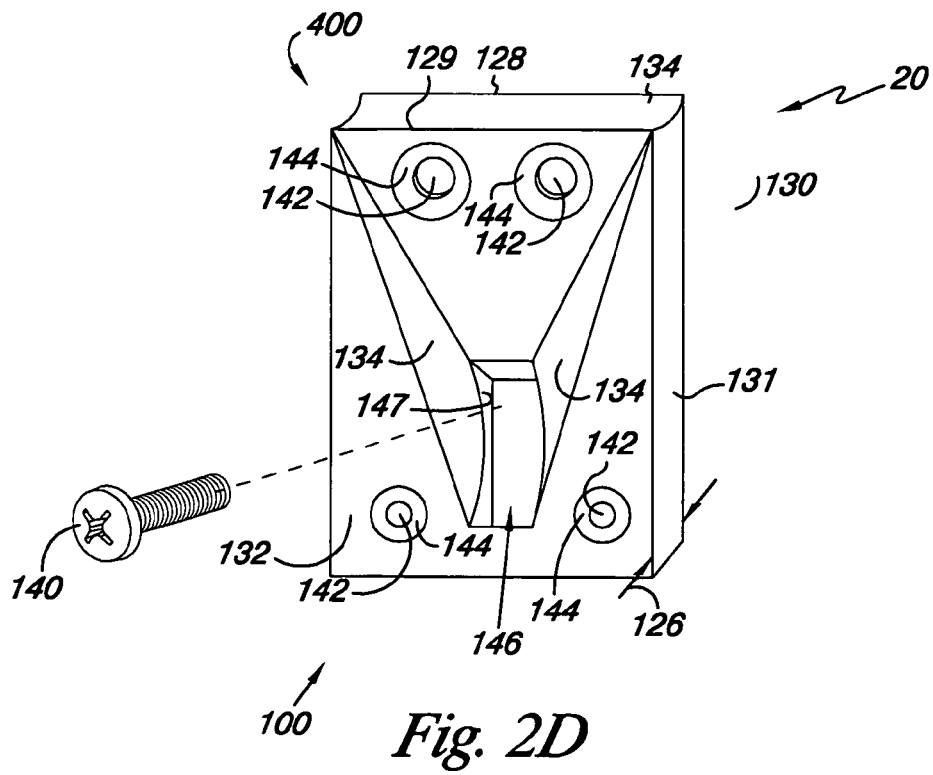
FIG. 2D illustrates a partial perspective view of an exemplary embodiment of an apparatus in accordance with the present inventions wherein the bone plate has a channel that receives a reduction wire and an aperture configured to engage a reduction wire mount.
Figure 2E:
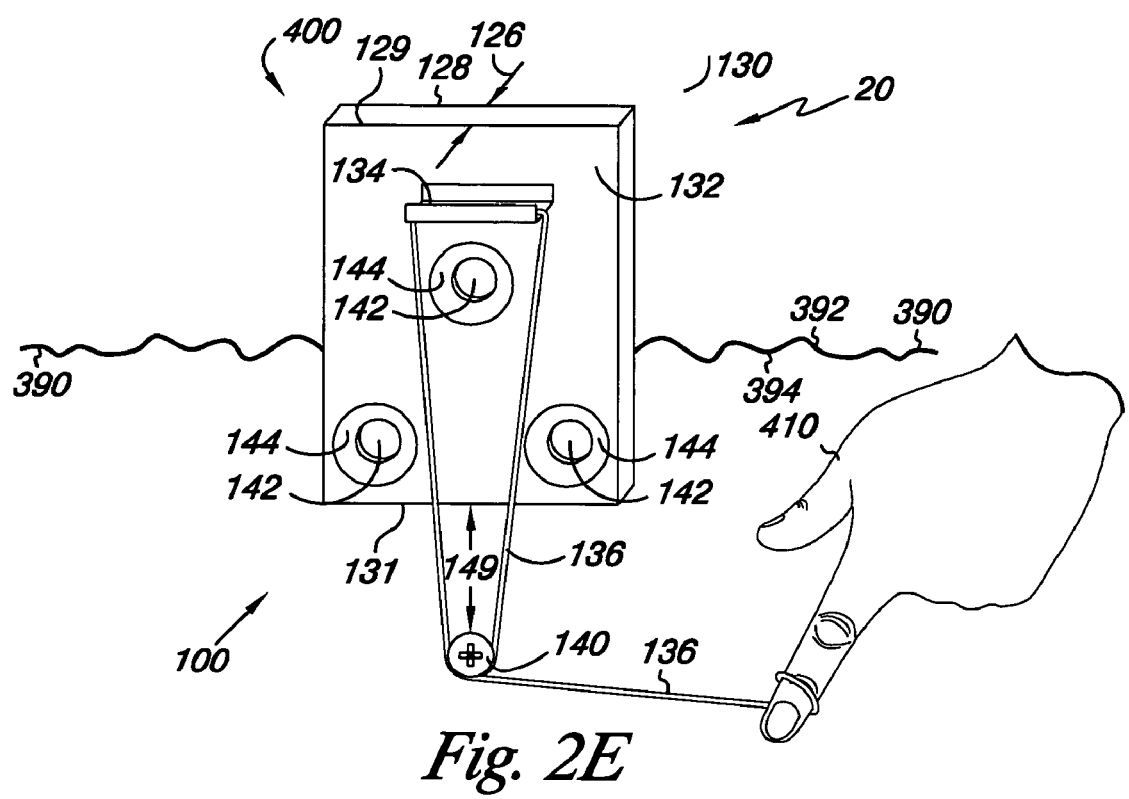
FIG. 2E illustrates a partial perspective view of an exemplary embodiment of an apparatus in accordance with the present inventions wherein the channel is configured as an appendage to the second surface.
Figure 3A:
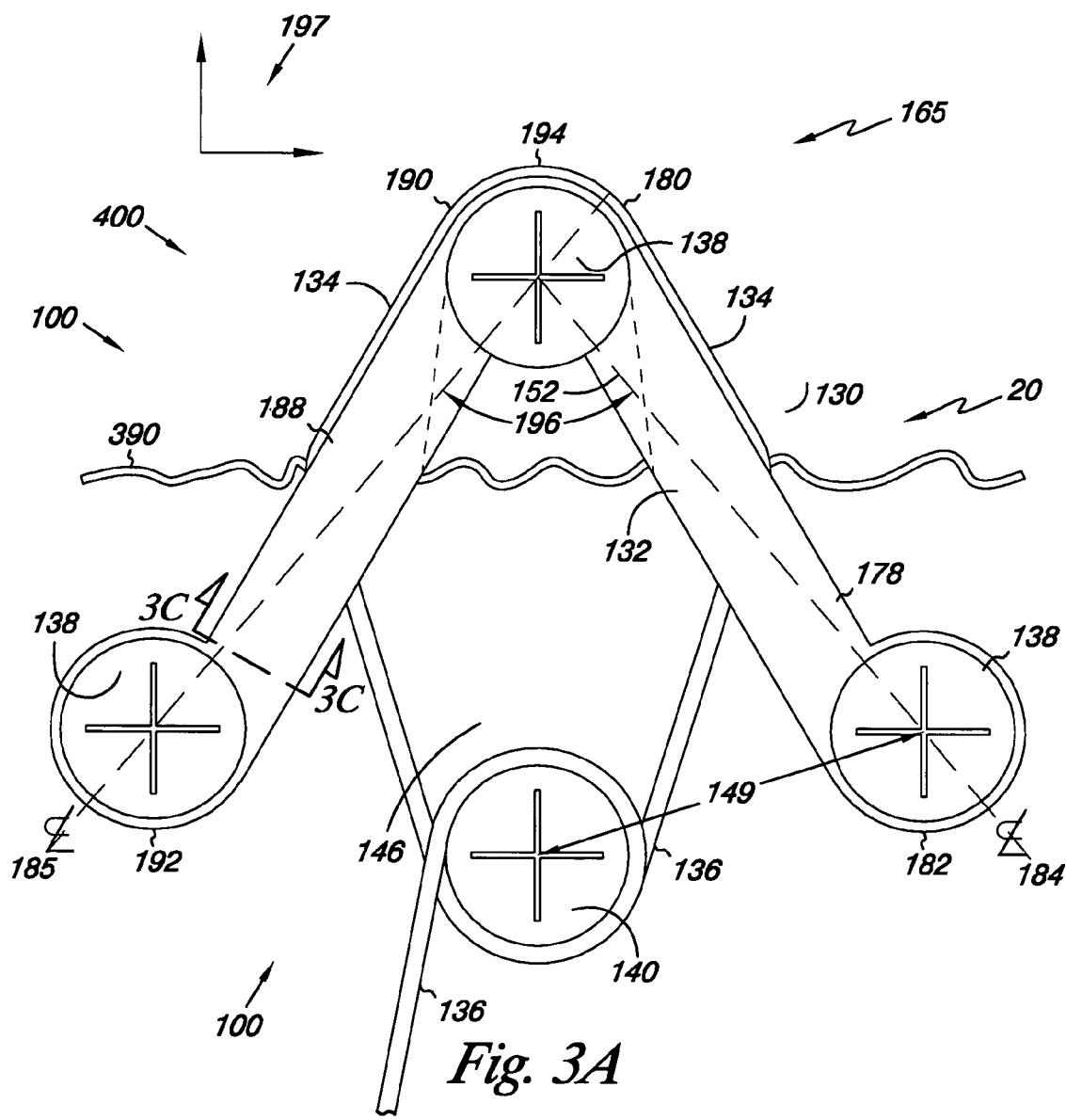
FIG. 3A illustrates a partial proximal perspective view of an exemplary embodiment of an apparatus in accordance with the present inventions wherein the bone plate is configured as a "V" shaped structure having a channel, thick regions that support reduction of a fracture, thin regions that provide flexibility, and an apron, and also showing a reduction wire, reduction wire mount, and fasteners.
Figure 3B:
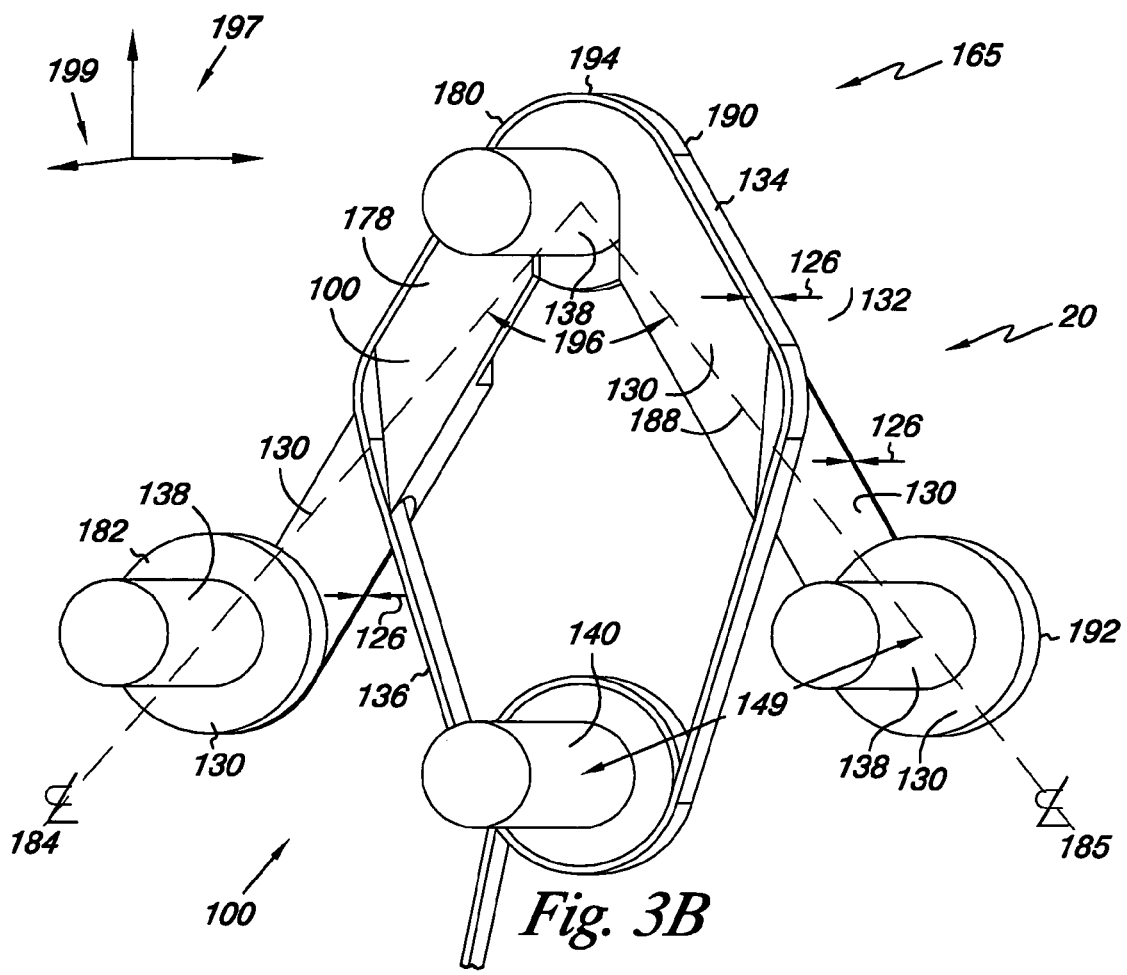
FIG. 3B illustrates a partial distal perspective view of an exemplary embodiment of an apparatus in accordance with the present inventions wherein the bone plate is configured as a "V" shaped structure having a channel, thick regions that support reduction of a fracture, thin regions that provide flexibility, and an apron, and also showing the reduction wire, reduction wire mount, and fasteners.
Figure 3C:
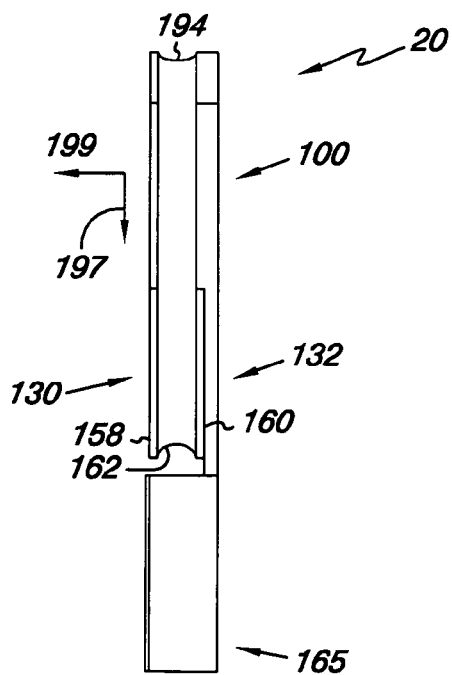
FIG. 3C illustrates a cross-sectional view of an exemplary embodiment of an apparatus in accordance with the present inventions wherein the bone plate is configured as a "V" shaped structure having a channel, thick regions that support reduction of a fracture, thin regions that provide flexibility, and an apron.
Figure 3D:
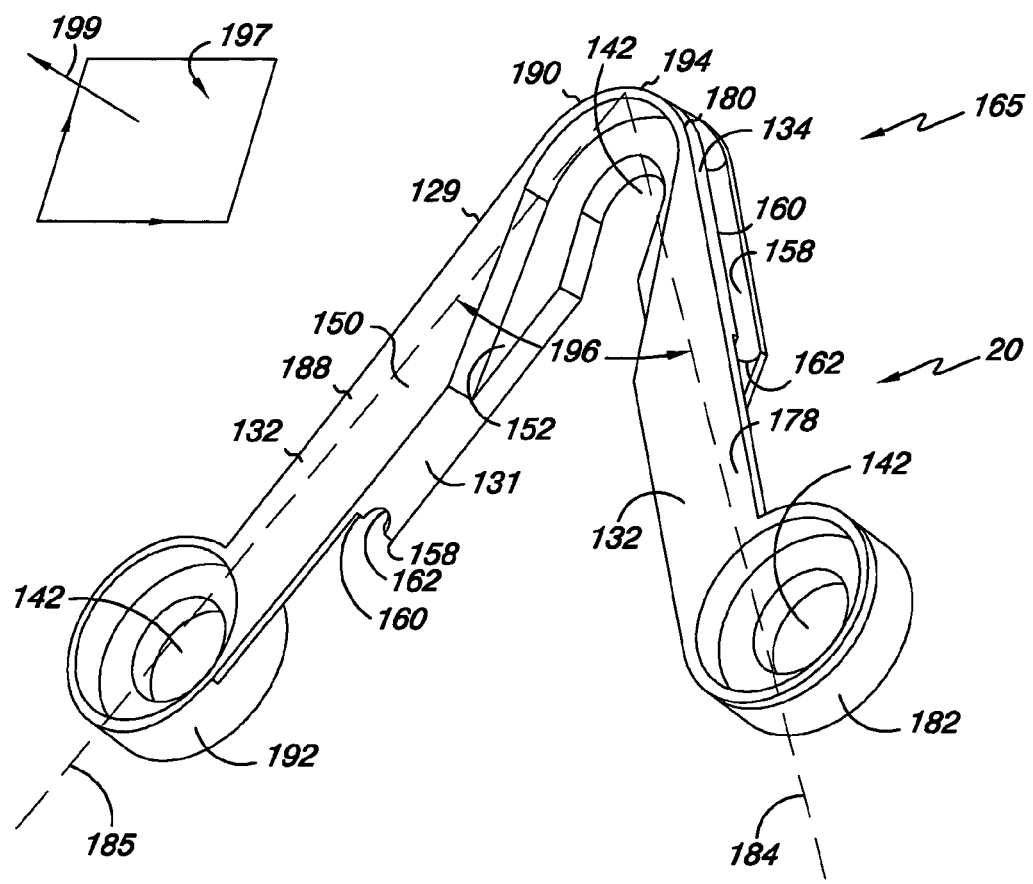
FIG. 3D illustrates a partial proximal perspective view of an exemplary embodiment of an apparatus in accordance with the present inventions wherein the bone plate is configured as a "V" shaped structure having a channel, thick regions that support reduction of a fracture, thin regions that provide flexibility, and an apron.
Figure 3E:
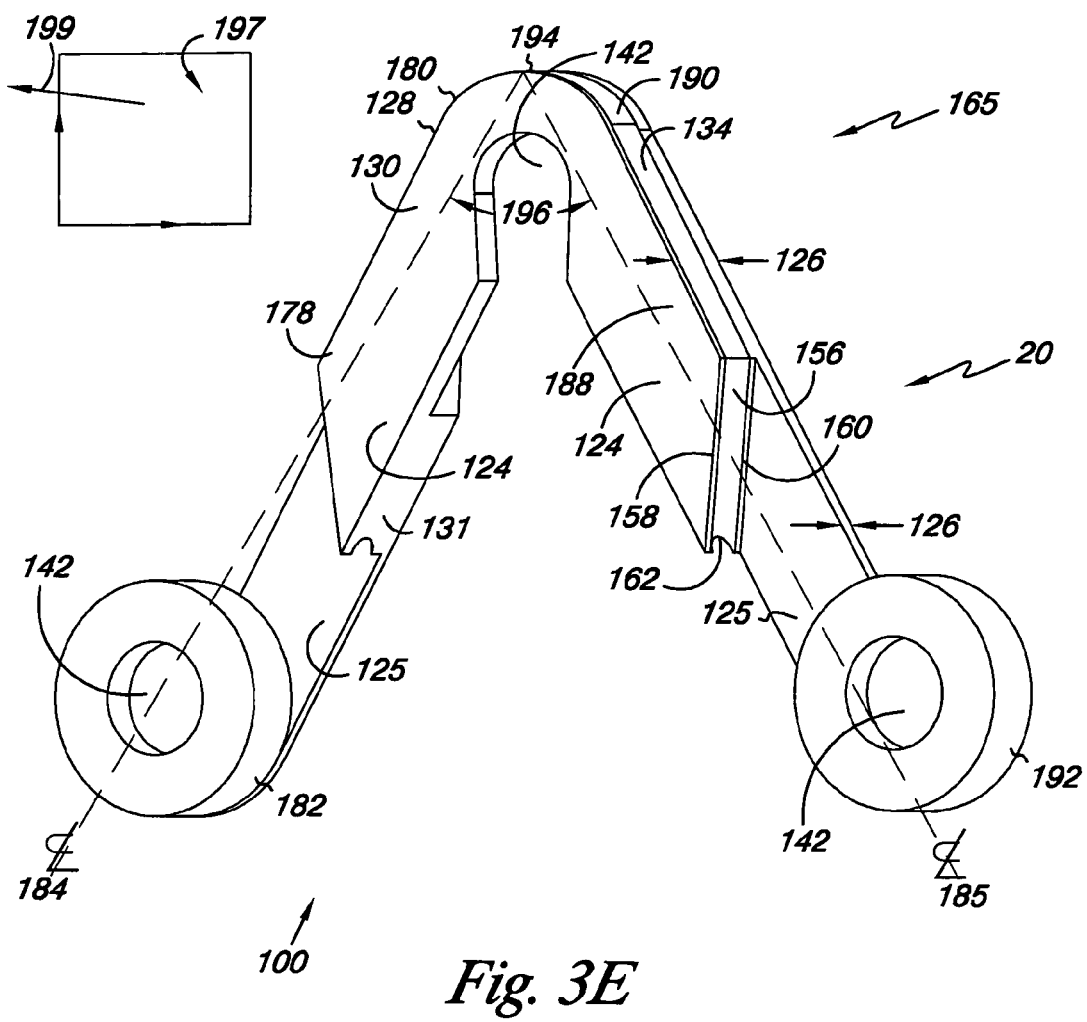
FIG. 3E illustrates a partial distal perspective view of an exemplary embodiment of an apparatus in accordance with the present inventions wherein the bone plate is configured as a "V" shaped structure having a channel, thick regions that support reduction of a fracture, thin regions that provide flexibility, and an apron; and, FIG. 4 illustrates an example of a compression opening in a portion of a bone plate and includes a bone screw with a countersink head.

The bone plate 100 is configured with a channel 134 that receives a reduction wire 136. A channel 134 that is designed to receive a reduction wire 136 may be configured in a portion of the peripheral surface 131 of the bone plate 100, as shown in FIGS. 2A and 2B. As shown in FIGS. 2C and 2D, the channel 134, may be may be configured in both a portion of the peripheral surface 131 and a portion of the second surface 132. At least a portion of the channel may be configured in the first surface 130. The channel 134 may be configured as an appendage to the bone plate 100, as shown in FIG. 2E. The bone plate 100 may be configured such that the channel 134 is formed by various cannula, lumen, or other hollow structures formed between the first surface 130 and the second surface 132. In various embodiments, such as those illustrated in FIGS. 2A-2E, the peripheral surface 131 may be recessed to receive a reduction wire 136, at least in part, by being interior to the first boundary 128 and the second boundary 129. The peripheral surface 131 may be substantially solid. However, in some embodiments, a series of posts or other discrete connectors may be used to link the first side 130 to the second side 132 so that the discrete connectors form a portion of the channel.

In some embodiments, as exemplified by FIG. 2C, a portion of the peripheral surface 131 may be configured to slideably receive or otherwise engage the reduction wire mount 140. The peripheral surface 131 may be configured to accommodate the reduction wire mount 140 such as a bone screw 220, for example, by being sized to bias against the reduction wire mount 140 while allowing the reduction wire mount 140 to slide. The peripheral surface may engage the reduction wire mount 140 upon tightening the reduction wire mount 140 so as to fasten the bone plate 100 to the bone surface 400.

In the embodiments exemplified by FIG. 2D, the bone plate 100 defines an aperture 146 having at least one aperture side 147, which may be configured to slideably receive or otherwise engage the reduction wire mount 140. The aperture 146 passes through the bone plate 100 between the first side 130 and the second side 132 within the first boundary 128 and the second boundary 129. The aperture 146 may be configured to accommodate the reduction wire mount 140 such as a bone screw 220, for example, by being sized to bias against the reduction wire mount 140 while allowing the reduction wire mount 140 to slide within the aperture and engaging the reduction wire mount 140 upon tightening the reduction wire mount 140 so as to anchor the bone plate 100 to the bone surface 400.

Another embodiment of an apparatus 20 according to the present invention is illustrated in FIGS. 3A-3E. In this embodiment, the bone plate 100 has a "V" shaped structure 165 with a first arm 178 and a second arm 188. The first arm 178 and the second arm 188 may be approximately the same length, as illustrated, or the first arm 178 and the second arm 188 may be of different lengths. The first arm 178 has a first end 180 and a second end 182, and the second arm 188 has a first end 190 and a second end 192. The bone plate 100 is formed by securing the first end 180 of the first arm 178 to the first end 190 of the second arm 188 thereby forming an apex 194. The first arm 178 is secured to the second arm 188 such that first arm 178 and the second arm 188 generally lie in a plane 197. The plane 197 of the "V" shaped structure 165 of the bone plate 100 defined by the first arm 178 and the second arm 188 generally conforms to the bone surface 400 so that the bone plate 100 may be fastened to the bone surface 400. A perpendicular 199 is defined with respect to the plane 197, and the perpendicular 199 is substantially perpendicular to the bone surface 400 when the bone plate 100 is fastened to the bone surface 400. The first arm 178 has a centerline 184 and the second arm has a centerline 185. The centerline 184 of the first arm 178 intersects the centerline 185 of the second arm 188 so that an angle 196 may be defined between the centerline 184 of the first arm 178 and the centerline 185 of the second arm 188.

In the embodiment illustrated by FIGS. 3A-3E, fastener opening 142 are located at the apex 194 and at the second end 182 of the first arm 178 and at the second end 182 of the second arm 188 so that the bone plate 100 may be affixed to the bone surface 400 by three fasteners 138. The fastener openings 142, as illustrated in this embodiment, are countersunk 144 in order to maintain a low profile of the bone plate 100 when installed. The bone plate 100 having a "V" shaped structure 165 may be variously configured with any suitable number of fastener openings 142 so that any suitable number of fasteners 138 may be used to fasten the bone plate 100 to the bone surface 400.

Additionally, the embodiment shown in FIGS. 3A-3E features an apron 152 located proximate the apex 194. The apron 152 is designed to be received under a fastener 138 and to be held by the fastener 138 when the fastener 138 is tightened to engage the apron 152. The surgeon may partially insert a fastener 138 such as a bone screw 220, and then slide the apron 152 under the fastener 138. After properly orientating the bone plate 100, the surgeon then tightens the fastener 138 to hold the bone plate 100 in position. The apron 152 thus eliminates the need for the surgeon to drill a hole in the bone, align a fastener opening 142 with a hole in the bone, and then insert a fastener 138, which can be difficult to accomplish.

The thickness 126 varies over different regions of the bone plate 100 having a "V" shaped structure 165, as illustrated in FIGS. 3A-3E, such that there are thick regions 124 and thin regions 125. The thick regions 124 have greater stiffness in the direction perpendicular 199 to the plane 197 of the bone plate 100 than the thin regions 125. The thick regions 124 of the bone plate 100 provide resistance to deflection to maintain fixation of a fracture 390 in the direction perpendicular 199 to the plane 197 of the bone plate. The thin regions 125 of the bone plate 100 are compliant in the direction perpendicular 199 to the plane 197 of the bone plate 100 in order to be conformable to surface curvature and surface irregularities of the bone surface 400. The compliance of the thin regions 125 of the bone plate 100 increases the ease of surgical attachment of the bone plate 100 to the bone surface 400.

The bone plate 100 having a "V" shaped structure 165, as illustrated in FIGS. 3A-3E, acts as an element of a truss and has stiffness in the plane 197 sufficient to support structurally the bone against stresses in the plane 197. Angles 196 characteristic of a truss would be 45° and 60°. Examples of stresses in the plane 197 of the bone plate 100 would include stresses produced by chewing when the bone plate 100 is fastened to a fractured mandibular bone 415.

The channel 134 in the embodiment of a bone plate 100 having a "V" shaped structure 165 illustrated in FIGS. 3A-3E is configured into a portion of the peripheral surface 131 of thick regions 124 of the bone plate 100 generally proximate the apex 194. The channel 134 is illustrated as having a first channel side 158, a second channel side 160, and a channel bottom 162. The first channel side 158 is distal and the second channel side 160 is proximal. The first channel side 158 and the second channel side 160 serve to retain the reduction wire 136 in the channel 134 when the surgeon applies tension to the reduction wire 136. The channel bottom 162, as illustrated in FIGS. 3A-3E, is curved to bias against the reduction wire 136 to retain the reduction wire 136, while allowing the reduction wire 136 to slide within the channel 134 along the curved channel bottom 162. The reduction wire 136 slides within the channel 134 when the surgeon applies tension to the reduction wire 136, which allows the bone plate 100 and the reduction wire mount 140 to move toward one another so as to bring the fracture 390 into reduction.

The channel 134, as illustrated in FIGS. 3A-3E is positioned proximate the first side 130 of the bone plate 100 so that the reduction wire 136 passes proximate to the first side 130 of the bone plate 100 to be proximate to the bone surface 400, so that the reduction wire 136 may be received by the reduction wire mount 140 proximate to the bone surface 400. By being proximate to the bone surface 400, the moment transmitted to the bone surface 400 by the tension force in the reduction wire 136 through the fasteners 138 of the bone plate 100 and through the reduction wire mount 140 is minimized. The first channel side 158 is configured such that the bone surface 400 is protected from contact with the reduction wire 136, although the reduction wire 136 is proximate the bone surface 400. This prevents damage to the bone surface 400 by the reduction wire 136.

Figure 4:
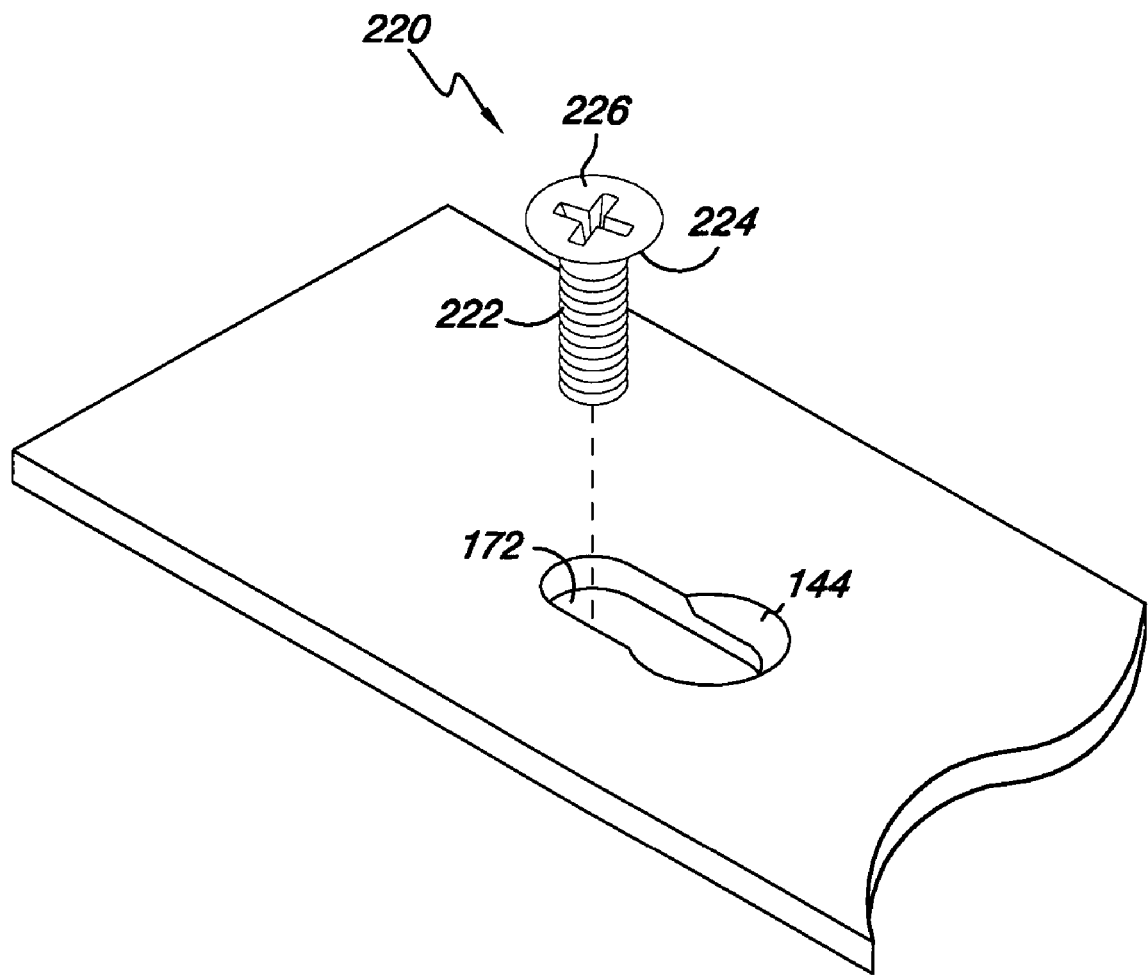

The bone plate 100 may, in various embodiments be configured with compression openings 172 for fastening by standard bone screws 220. An example of a compression opening 172 in a portion of a bone plate 100 is illustrated in FIG. 4. Those skilled in the art understand the design of compression openings 172 and the mechanism by which compression openings 172 function.

In operating a device 20 to reduce and fixate a fracture 390, the bone plate 100 is fastened to the bone surface 400 on a first fracture side 392 of the fracture 390. The bone plate 100 is positioned such that the bone plate 100 will span the fracture 390 so that the bone plate 100 may be fastened to the second fracture side 394 upon reduction of the fracture 390.

The first fracture side 392 for placement of the bone plate 140 and the second fracture side 394 for placement of the reduction wire mount 140 are chosen such that the second fracture side 394 is compressed against the first side 130 of the bone plate 100 when the bone plate 100 is fastened to the bone surface 400 on the first fracture side 392 so that fastening the bone plate 100 to the bone surface 400 on the first fracture side 392 serves to reduce the fracture 390 in the direction perpendicular 199 to the bone plate 100.

For example, when the apparatus 20 is used to treat a mandibular fracture, the bone plate 100 is fastened to the buccal-labial (cheek or lip) bone surface 400 of the mandibular bone 415. The side of the fracture 390 having the greater lingual (tongue side) displacement is designated as the first fracture side 392, and the bone plate 100 is fastened to the first fracture side 392. Fastening the bone plate 100 to the first fracture side 392 then forces the second fracture side 394 in the labial direction thereby reducing the buccal—lingual displacement of the fracture 390.

If a bone plate 100 having a "V" shaped structure 165, as illustrated in FIG. 3A-3E, is used, the thick region 124 of the bone plate 100 should engage the bone on both the first fracture side 392 and the second fracture side 394. This thick region 124 of the bone plate 100, as illustrated in FIGS. 3A-3E, should be sized to have the stiffness necessary to reduce the fracture 390 in the direction perpendicular 199 to the bone plate 100.

If an embodiment of the apparatus 20 having an apron 152, as shown, for example, in FIGS. 3A-3E, is utilized, a fastener 138 is placed in the first fracture side 392. The bone plate 100 is oriented so that the first surface 130 is distal to the bone surface 400. The apron 152 is then slid under the fastener 138 so that the apron 152 receives and engages the fastener 138. If necessary, the fastener 138 is further tightened so that the fastener 138 engages the apron 152. The bone plate 100 should be positioned so that the bone plate 100 may be fastened to the second fracture side 394 following reduction of the fracture 390. Embodiments lacking an apron 152 would be fastened in ordinary ways as recognized by those skilled in the art.

After the bone plate 100 is properly positioned and mounted to the bone surface 400, a reduction wire mount 140 is mounted to the second fracture side 394 of the fracture 390. The reduction wire mount 140 should be properly mounted with respect to the bone plate 100. For example, in some embodiments, such as those shown in FIGS. 2C and 2D, the bone plate 100 may be designed to slideably receive or otherwise engage the reduction wire mount 140, so that the reduction wire mount should be mounted to engage the bone plate 100. The reduction wire mount 140 should be mounted to avoid direct engagement with bone plates 100 that are designed to function without direct engagement with the reduction wire mount 140. The reduction wire mount 140 should also be located so that the reduction wire 136 will be substantially perpendicular to the fracture 390 when the reduction wire 136 is received by the channel 134 and received by the reduction wire mount 140.

Following placement of the bone plate 100 and the reduction wire mount 140, a reduction wire 136 is fastened to the reduction wire mount 140 and received by the channel 134 on the bone plate 100. The bone plate 100 should be oriented so that a force applied to the reduction wire 136 will draw the bone plate toward the reduction wire mount 140, and, hence, reduce the fracture 390. Then, tension is applied to the reduction wire 136, typically by a surgeon pulling on the reduction wire 136, to reduce the fracture 390 by drawing the first fracture side 392 and the second fracture side 394 of the fracture 390 together. Finally, the bone plate 100, which now spans the reduced fracture 390, is fastened to the bone on the second fracture side 394 of the fracture 390 by one or more fasteners 138 to fixate the fracture 390. If an embodiment of the apparatus 20 as illustrated in FIGS. 3A-3E is utilized, the thin regions 125 of the bone plate 100 are able to flex to facilitate fastening to curved or irregular bone surfaces 400. The bone plate 100 may include compression openings 172 corresponding to the second fracture side 394, so that fastening the bone plate 100 to the bone surface 400 on the second fracture side 394 via the compression openings 172 and appropriate fasteners 138 would further reduce the fracture 390.

In some embodiments, the reduction wire 136 may be removed after the bone plate 100 has been fastened to the bone surface 400 on the first fracture side 392 and the second fracture side 394. Some embodiment may use the reduction wire mount to secure the bone plate 100 to the bone surface 400 on the second fracture side 394. In other embodiments, the reduction wire 136 and the reduction wire mount 140 may be removed following fastening the bone plate 100 to the bone surface 400 on the first fracture side 392 and to the bone surface 400 on the second fracture side 394. The reduction wire 136 and the reduction wire mount 140 may remain following fastening the bone plate 100 to the first fracture side 392 and to the second fracture side 394 in order to provide additional stability to the fixated fracture 390.

The foregoing discussion discloses and describes merely exemplary embodiments of the present invention. It should be understood that no limitation of the scope of the invention is intended thereby. Upon review of the specification, one skilled in the art will readily recognize from such discussion, and from the accompanying drawings and claims, that various changes, modifications and variations can be made therein without departing from the spirit and scope of the inventions as defined in the following claims.

We claim:

1. An apparatus for the reduction and fixation of a fractured bone designed for use in cooperation with a reduction wire and configured for use in cooperation with a reduction wire mount, comprising:
    a bone plate, the bone plate defining;
        a first surface, whereby when the bone plate is in use the first surface is distal to a bone surface and configured to be biased against the bone surface;
        a second surface, whereby when the bone plate is in use the second surface is proximal to the bone surface;
        a first perimeter bounding the first surface;
        a second perimeter bounding the second surface;
        a peripheral surface defined by a portion of the bone plate joining the first perimeter and the second perimeter, the peripheral surface defining a plurality of sides;
        a plurality of fastener openings disposed between the first surface and the second surface so that the bone plate may be secured to the bone surface by a plurality of fasteners; and
        a channel defined along at least one side of the peripheral surface, the channel being configured to receive and slideably retain a reduction wire.

2. The apparatus of claim 1, wherein the bone plate further defines a slot passing between the first surface and the second surface and defined by a portion of the peripheral surface.

3. The apparatus of claim 2, wherein the channel is formed in a first side of the plurality of sides and the slot is formed in a second side of the plurality of sides.

4. The apparatus of claim 2, wherein the first surface and the second surface comprise an interior portion interior of the first perimeter and the second perimeter and the slot is located in the interior portion and passes between the first surface and the second surfaces, the slot being sized to receive and bias against a wire reduction mount.

5. The apparatus of claim 1, wherein the bone plate further defines a slot passing between the first surface and the second surface and defined by a portion of the peripheral surface, the slot having a first radius defined by opposing portions of the first surface and a second radius defined by opposing portions of the second surface, the first radius and second radius being of a suitable dimension to receive a reduction wire mount.

6. The apparatus of claim 1, the channel being dimensioned to receive and at least partially enclose a reduction wire, thus protecting a bone surface from the reduction wire when the reduction wire is received by the channel.

7. The apparatus of claim 1, further comprising: an apron configured to be received by a fastener and held by the fastener when the fastener is tightened to engage the apron.

8. The apparatus of claim 1, further comprising a reduction wire mount; and, a reduction wire, the reduction wire received by the channel and the reduction wire received by the reduction wire mount.

9. The apparatus of claim 1, further comprising: at least one fastener opening configured as a compression opening, the compression opening oriented to increase reduction of a bone fracture as the fastener is tightened.

10. The apparatus of claim 1, wherein the first surface and the second surface comprise an interior portion interior of the first perimeter and the second perimeter, the first and second surfaces defining a plurality of branches extending from the interior portion, wherein the branches comprise a portion having a reduced thickness between the first and second surfaces compared with the interior portion.

11. The apparatus of claim 1, wherein the channel extends around at least two of the plurality of sides.

12. An apparatus for the reduction and fixation of a fractured bone designed for use in cooperation with a reduction wire and configured for use in cooperation with a reduction wire mount, comprising:
    a bone plate, the bone plate defining;
        a first surface, whereby when the bone plate is in use the first surface is distal to a bone surface and configured to be biased against the bone surface;
        a second surface, whereby when the bone plate is in use the second surface is proximal to the bone surface;
        a first perimeter bounding the first surface;
        a second perimeter bounding the second surface;
        a peripheral surface defined by a portion of the bone plate joining the first perimeter and the second perimeter;
        an interior portion of the first and second surfaces distal to the peripheral surface;
        a plurality of fastener openings disposed in the interior portion between the first surface and the second surface so that the bone plate may be secured to the bone surface by a plurality of fasteners; and, an aperture passing between the first surface and the second surface and defined by a portion of the peripheral surface, the aperture sized to receive a reduction wire mount.

13. The apparatus of claim 12, wherein the aperture has a first radius defined by opposing portions of the first surface and a second radius defines by opposing portions of the second surface, the first and second radius being of a suitable dimension to receive a reduction wire mount.

14. The apparatus of claim 12, wherein the bone plate further defines a channel defined along at least a portion of the peripheral surface, the channel being configured to receive and slideably retain a reduction wire.

15. An apparatus for the reduction and fixation of a fractured bone designed for use in cooperation with a reduction wire and configured for use in cooperation with a reduction wire mount, comprising:
   a bone plate, the bone plate defining;
      a first surface, whereby when the bone plate is in use the first surface is distal to a bone surface and configured to be biased against the bone surface;
      a second surface, whereby when the bone plate is in use the second surface is proximal to the bone surface;
      a first perimeter bounding the first surface;
      a second perimeter bounding the second surface;
      a peripheral surface defined by a portion of the bone plate joining the first perimeter and the second perimeter;
      an interior portion of the first and second surfaces distal to the peripheral surface;
      a plurality of fastener openings disposed in the interior portion between the first surface and the second surface so that the bone plate may be secured to the bone surface by a plurality of fasteners; and,
      an aperture located in the interior portion and passing between the first surface and the second surfaces, the aperture sized to receive and bias against a reduction wire mount.

16. The apparatus of claim 15, wherein the aperture has a first radius defined by opposing portions of the first surface and a second radius defines by opposing portions of the second surface, the first and second radius being of a suitable dimension to receive a reduction wire mount.

17. The apparatus of claim 15, wherein the bone plate further defines a channel defined along at least a portion of the peripheral surface, the channel being configured to receive and slideably retain a reduction wire.

* * * * *